US012386318B2

(12) United States Patent
Park et al.

(10) Patent No.: US 12,386,318 B2
(45) Date of Patent: Aug. 12, 2025

(54) ELECTRONIC DEVICE INCLUDING BIOMETRIC RECOGNIZING MODULE

(71) Applicant: Samsung Electronics Co., Ltd., Gyeonggi-do (KR)

(72) Inventors: Jihoon Park, Gyeonggi-do (KR); Hyunwoo Kim, Gyeonggi-do (KR); Jihun Heo, Gyeonggi-do (KR); Seungho Hwang, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 629 days.

(21) Appl. No.: 17/748,174

(22) Filed: May 19, 2022

(65) Prior Publication Data

US 2022/0413449 A1    Dec. 29, 2022

Related U.S. Application Data

(63) Continuation of application No. PCT/KR2022/006657, filed on May 10, 2022.

(30) Foreign Application Priority Data

Jun. 28, 2021  (KR) .................. 10-2021-0083705

(51) Int. Cl.
*G06V 40/13*        (2022.01)
*G04G 17/04*        (2006.01)
(Continued)

(52) U.S. Cl.
CPC .......... *G04G 21/025* (2013.01); *G04G 17/04* (2013.01); *G06F 21/32* (2013.01);
(Continued)

(58) Field of Classification Search
CPC ......... G06V 40/13; G04G 21/02; G04G 17/04
See application file for complete search history.

(56) References Cited

U.S. PATENT DOCUMENTS 9,779,277 B2   10/2017  Ohtsuka et al.
10,057,470 B2   8/2018  Kim et al.
(Continued)

FOREIGN PATENT DOCUMENTS

CH           716923 A2    6/2021
CN        105045085 A    11/2015
(Continued)

OTHER PUBLICATIONS

US 10,222,753 B1, 03/2019, Ely (withdrawn)
Extended European Search Report dated Sep. 11, 2024.
International Search Report dated Aug. 18, 2022.

*Primary Examiner* — Joseph R Haley
(74) *Attorney, Agent, or Firm* — Cha & Reiter, LLC

(57) ABSTRACT

According to certain embodiments, an electronic device comprises: a housing; a protrusion from a side surface of the housing including a first window and a second window; a first board disposed inside the housing; a second board connected to one surface of the first board; a first sensor circuit mounted on a first surface of the second board, disposed in the protrusion, and spaced apart from and under the first window; and a second sensor circuit mounted on a second surface of the second board facing in a direction opposite to the first surface of the second board, disposed in the protrusion, and spaced apart from and above the second window.

20 Claims, 10 Drawing Sheets

(51) Int. Cl.
   *G04G 21/02*    (2010.01)
   *G06F 21/32*    (2013.01)
   *G06V 40/10*    (2022.01)
   *G06V 40/12*    (2022.01)

(52) U.S. Cl.
   CPC ...... *G06V 40/1318* (2022.01); *G06V 40/1365* (2022.01); *G06V 40/15* (2022.01)

(56) References Cited

U.S. PATENT DOCUMENTS

| | | | |
|---|---|---|---|
| 10,157,590 B1* | 12/2018 | Aflatooni | G09G 5/10 |
| 10,318,958 B2 | 6/2019 | Kim | |
| 10,594,026 B2 | 3/2020 | Choi et al. | |
| 10,866,619 B1* | 12/2020 | Bushnell | G06F 1/169 |
| 10,962,935 B1 | 3/2021 | Ely et al. | |
| 11,354,933 B2 | 6/2022 | Lee et al. | |
| 2016/0091922 A1* | 3/2016 | Nazzaro | G04C 10/00 |
| | | | 307/104 |
| 2016/0241553 A1 | 8/2016 | Kim | |
| 2017/0090599 A1 | 3/2017 | Kuboyama et al. | |
| 2017/0323130 A1* | 11/2017 | Dickinson | G06V 40/1306 |
| 2018/0181733 A1 | 6/2018 | Shim et al. | |
| 2020/0041962 A1 | 2/2020 | Beyhs | |
| 2022/0230011 A1* | 7/2022 | Wan | G06V 40/1318 |

FOREIGN PATENT DOCUMENTS

| | | |
|---|---|---|
| CN | 209950520 U | 1/2020 |
| JP | 2002-323581 A | 11/2002 |
| KR | 10-2016-0101497 A | 8/2016 |
| KR | 10-2017-0053385 A | 5/2017 |
| KR | 10-2021-0021657 A | 3/2021 |

\* cited by examiner

ELECTRONIC DEVICE INCLUDING BIOMETRIC RECOGNIZING MODULE

CROSS-REFERENCE TO RELATED APPLICATION(S)

This application is a continuation application, claiming priority under § 365(c), of an International application No. PCT/KR2022/006657, filed on May 10, 2022, which is based on and claims the benefit of a Korean patent application number 10-2021-0083705, filed on Jun. 28, 2021, in the Korean Intellectual Property Office, the disclosure of which is incorporated by reference herein in its entirety.

BACKGROUND

Field

Certain embodiments of the disclosure relate to an electronic device including a biometric recognition module.

Description of Related Art

Wearable electronic devices, such as a smartwatch are commonplace. The wearable electronic devices are providing increasing numbers of functions.

To measure a user's biometric information, various sensors may be mounted in the wearable electronic device. However, the positioning of the sensors raises several complications. For example, measuring biometric information through sensors on the front of the wearable electronic device may be difficult because of the front glass. The front glass may be thick for sturdiness, and hence measuring biometric information through sensors mounted in an in-display form may deteriorate in performance. When sensors are stacked adjacent to the rear plate of the wearable device, it may be difficult to keep the wearable electronic device thin.

In certain embodiments of the disclosure, an electronic device may include a protrusion from the side of the electronic device. The protrusion can include a placement space where a plurality of biometric sensors are disposed. The biometric sensors are capable of measuring user's biometric information.

SUMMARY

According to certain embodiments, an electronic device comprises: a housing; a protrusion from a side surface of the housing including a first window and a second window; a first board disposed inside the housing; a second board connected to one surface of the first board; a first sensor circuit mounted on a first surface of the second board, disposed in the protrusion, and spaced apart from and under the first window; and a second sensor circuit mounted on a second surface of the second board facing in a direction opposite to the first surface of the second board, disposed in the protrusion, and spaced apart from and above the second window.

According to certain embodiments, an electronic device comprises: a housing; a protrusion from a side surface of the housing including a first window and a second window; a first board disposed inside the housing; a second board connected to one surface of the first board, and including a first surface, a second surface in a direction perpendicular to the first surface, and a third surface in a direction opposite to the first surface; a first sensor circuit mounted on the second surface of the second board and disposed inside the protrusion, wherein the first window is spaced apart on a side of the first sensor circuit; and a second sensor circuit mounted on the third surface of the second board, and disposed inside the protrusion, wherein the second window is spaced part and under the second sensor circuit.

According to certain embodiments, an electronic device comprises: a housing; a protrusion from a side surface of the housing including a first window and a second window; a first board disposed inside the housing; a second board connected to one surface of the first board; a third board electrically connected to the second board through a plurality of connection members; a first sensor circuit disposed on a first surface of the third board, and wherein the first window is spaced apart above the first sensor circuit; and a second sensor circuit disposed on a second surface of the third board, and wherein the second window disposed to be spaced apart under the second sensor circuit.

DETAILED DESCRIPTION

In certain embodiments of the disclosure, the electronic device is provided with a plurality of biometric sensors capable of measuring user's biometric information disposed in the placement space of a biometric recognition module formed to protrude from the side of the electronic device, which not only improves the accuracy of biometric recognition but also enables slimming of the electronic device.

A wearable electronic device can include sensors for that provide biometric information, where the sensors have good performance, while maintaining the slimness of the housing. The wearable electronic device includes a protrusion from the housing. Since the protrusion might not include any portion of the display, the cover may be thinner, thereby allowing sensors facing the front to provide good performance. Additionally, since the protrusion is separate from the remaining body, the sensors that are inside the protrusion do not makes the wearable electronic device thicker.

FIG. 1-4 describe the wearable electronic device, the housing, and various internal components.

Electronic Device

Figure 1:
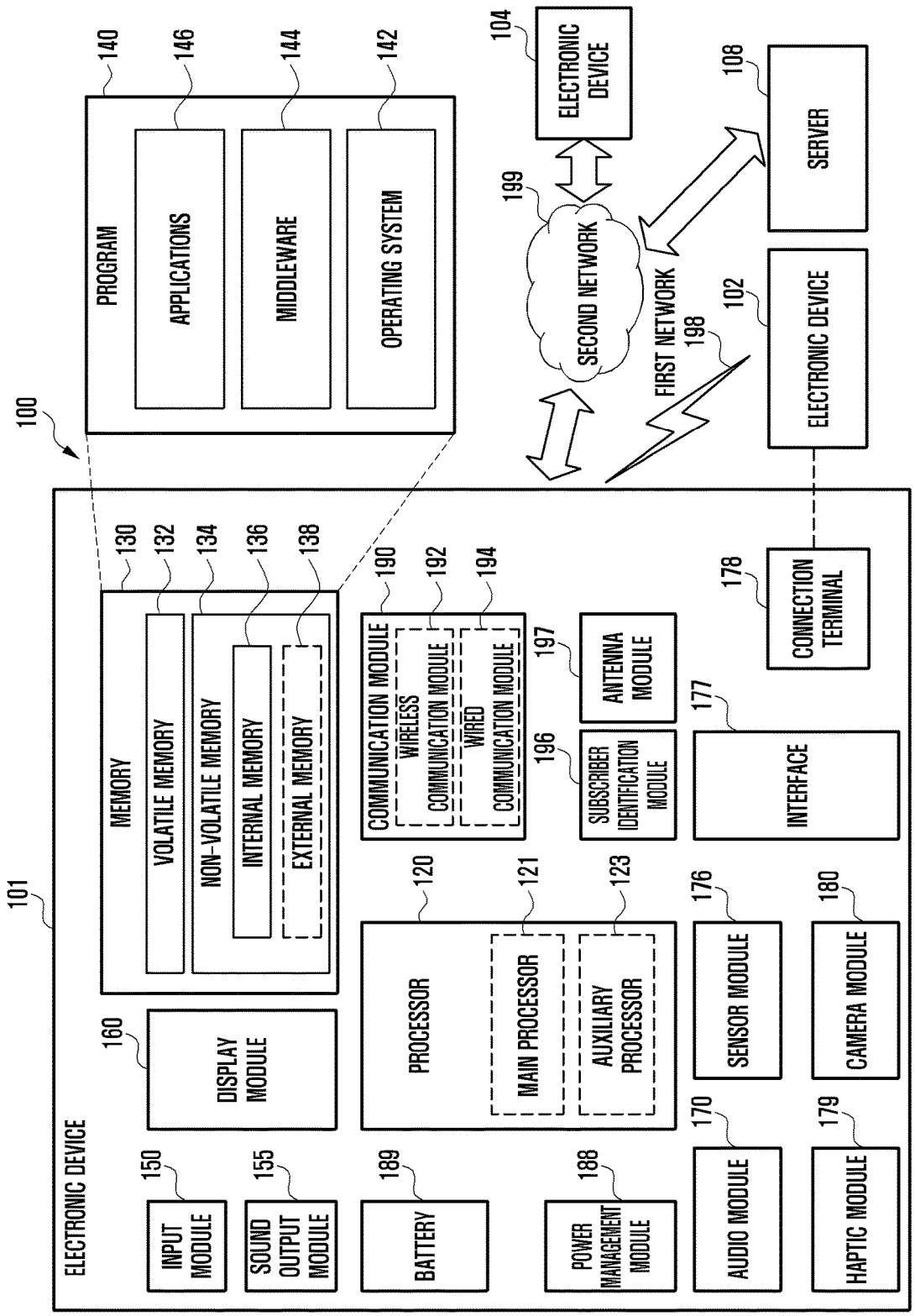
FIG. 1 is a block diagram of an electronic device in a network environment according to certain embodiments.

FIG. 1 is a block diagram illustrating an electronic device 101 in a network environment 100 according to certain embodiments. The electronic device 101 can include a wearable electronic device.

Referring to FIG. 1, an electronic device 101 in a network environment 100 may communicate with an electronic device 102 via a first network 198 (e.g., a short-range wireless communication network), or at least one of an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connection terminal 178, a haptic module 179, a camera module 180, a power management module 188, a battery 189, a communication module 190, a subscriber identification module (SIM) 196, or an antenna module 197. In some embodiments, at least one of the components (e.g., the connection terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The term "processor" shall be understood to refer to both the singular and plural contexts in this document.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134. The non-volatile memory 134 may include an internal memory 136 and/or an external memory 138.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) (e.g., speaker or headphone) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., through wires) or wirelessly. According to an embodiment, the interface 177 may include, for example, a high-definition multimedia interface (HDMI), a universal serial bus (USB) interface, a secure digital (SD) card interface, or an audio interface.

The connection terminal 178 may include a connector via which the electronic device 101 may be physically connected with the external electronic device (e.g., the electronic device 102). According to an embodiment, the connection terminal 178 may include, for example, an HDMI connector, a USB connector, an SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., an application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, Wi-Fi direct, or infrared data association (IrDA)) or the second network 199 (e.g., a long-range communication network, such as a legacy cellular network, a fifth generation (5G) network, a next-generation communication network, the Internet, or a computer network (e.g., LAN or wide area network (WAN))). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large-scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to certain embodiments, the antenna module 197 may form mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., an mmwave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

The electronic device according to certain embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that certain embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively," as "coupled with," "coupled to," "connected with," or "connected to" another element (e.g., a second element), it means that the element may be coupled with the other element directly (e.g., through wires), wirelessly, or via a third element.

As used in connection with certain embodiments of the disclosure, the term "module" may include a unit implemented in hardware, software, or firmware, and may interchangeably be used with other terms, for example, "logic," "logic block," "part," or "circuitry." A module may be a single integral component, or a minimum unit or part thereof, adapted to perform one or more functions. For example, according to an embodiment, the module may be implemented in a form of an application-specific integrated circuit (ASIC).

Certain embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities, and some of the multiple entities may be separately disposed in different components. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

In certain embodiments, the electronic device is a wearable electronic device that includes a sensor module 176. However, as will be shown in FIGS. 2 and 3, the wearable electronic device includes protrusion. The sensor module 176 can be disposed in the protrusion. Since the protrusion is separate from the display module 160 surface, the cover may be thinner. This allows improved performance by sensors facing the front of the wearable electronic device. Additionally, sensors can face the rear without increasing the thickness of the electronic device.

Housing

Figure 2:
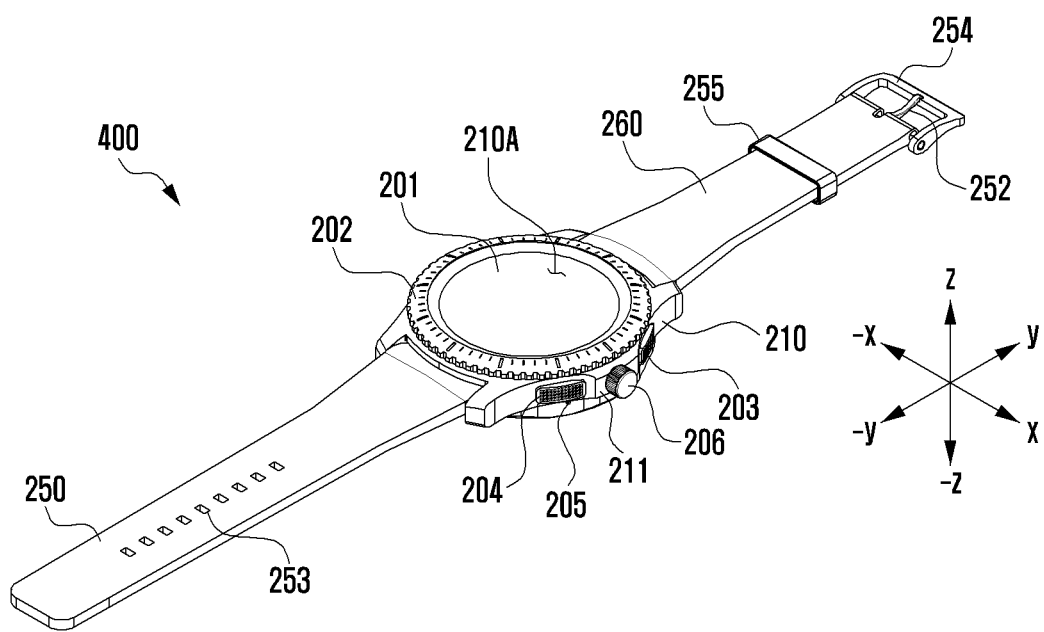
FIG. 2 is a front perspective view of an electronic device according to certain embodiments.
Figure 3:
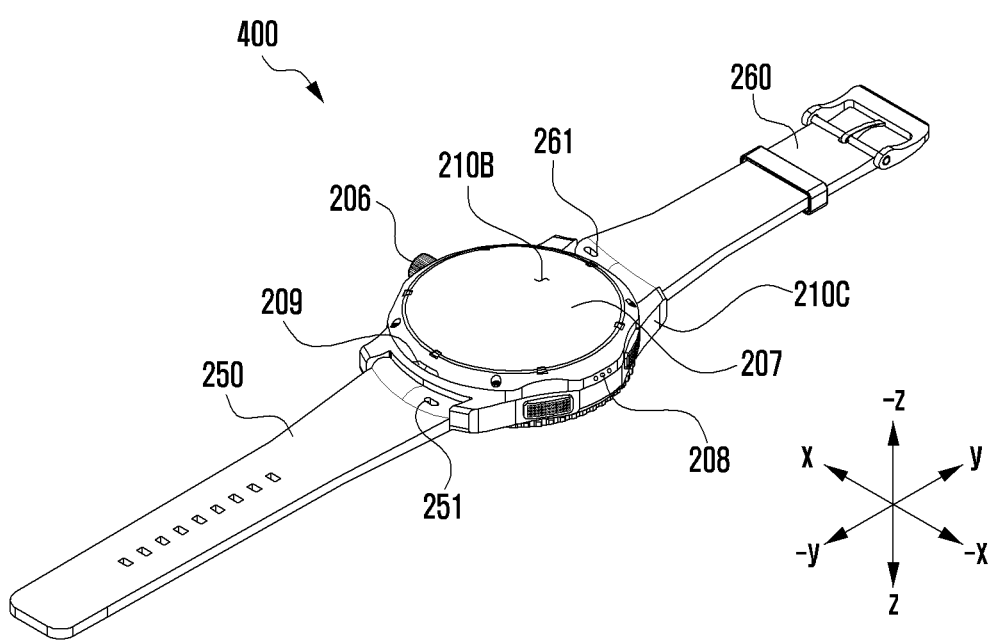
FIG. 3 is a rear perspective view of the electronic device of FIG. 2 according to certain embodiments.

FIG. 2 is a front perspective view of an electronic device 400 according to certain embodiments. FIG. 3 is a rear perspective view of the electronic device 400 of FIG. 2 according to certain embodiments. The wearable electronic device 400 includes protrusion 206. The sensors capable of providing biometric information can be disposed in the protrusion 206.

With reference to FIGS. 2 and 3, in one embodiment, the electronic device 400 may include a housing 210 including a first surface (or, front surface) 210A, a second surface (or, rear surface) 210B, and a side surface 210C surrounding the space between the first surface 210A and the second surface 210B, and fastening members 250 and connected to at least a portion of the housing 210 and configured to detachably fasten the electronic device 400 to a body part (e.g., wrist, ankle, etc.) of the user. In another embodiment (not shown), the housing 210 may refer to a structure forming some of the first surface 210A, the second surface 210B, and the side surface 210C in FIG. 2. In one embodiment, the first surface 210A may be formed by a front plate 201 that is substantially transparent at least in part (e.g., glass plate containing various coating layers, or polymer plate). The second surface 210B may be formed by a rear plate 207 that is substantially opaque. The rear plate 207 may be made of, for example, coated or colored glass, ceramic, polymer, metal (e.g., aluminum, stainless steel (STS), or magnesium), or a combination thereof. The side surface 210C is coupled to the front plate 201 and the rear plate 207 and may be formed by a side bezel structure (or, side member) 211 containing metal and/or polymer. In a certain embodiment, the rear plate 207 and the side bezel structure 211 may be integrally formed and contain the same material (e.g., metal material such as aluminum). The fastening members 250 and 260 may be made of various materials and formed in various shapes. The fastening members 250 and 260 may be formed as a single body or as plural unit links that are movable with each other, by woven material, leather, rubber, urethane, metal, ceramic, or a combination thereof.

In one embodiment, the electronic device 400 may include at least one of a display (e.g., display 220 in FIG. 4), an audio module 205 and 208, a sensor module, key input devices 202, 203 and 204, or a connector hole 209. In a certain embodiment, at least one of the components (e.g., key input device 202, 203 and 204, connector hole 209) may be removed from the electronic device 400, or a different component may be added to the electronic device 400.

The display 220 can be viewed through, for example, a significant portion of the front plate 201. The display 220 may have a shape corresponding to the shape of the front plate 201 and may have one of various shapes such as a circle, an ellipse, and a polygon. The display 220 may be disposed in combination with or adjacent to a touch sensing circuit, a pressure sensor capable of measuring the intensity (pressure) of a touch.

The audio module 205 and 208 may include a microphone hole 205 and a speaker hole 208. In the microphone hole 205, a microphone for picking up external sounds may be disposed therein, and plural microphones may be arranged to sense the direction of sound in a certain embodiment. The speaker hole 208 can be used for an external speaker and a call receiver. In a certain embodiment, the speaker hole 208 and the microphone hole 205 may be implemented as a single hole, or a speaker (e.g., piezo speaker) may be included without the speaker hole 208.

The sensor module may generate an electrical signal or data value corresponding to an internal operating state of the electronic device 400 or an external environmental state. The sensor module may include, for example, a biometric sensor module (e.g., fingerprint sensor and/or HRM sensor). The electronic device 400 may further include a sensor module (not shown) including at least one of, for example, a gesture sensor, a gyro sensor, an air pressure sensor, a magnetic sensor, an acceleration sensor, a grip sensor, a color sensor, an infrared (IR) sensor, a biometric sensor, a temperature sensor, a humidity sensor, or an illuminance sensor.

The key input devices 202, 203 and 204 may include a wheel key 202 disposed on the first surface 210A of the housing 210 and rotatable in at least one direction, and/or side key buttons 203 and 204 disposed on the side surface 210C of the housing 210. The wheel key may have a shape corresponding to the shape of the front plate 201. In another embodiment, the electronic device 400 may not include some or all of the key input devices 202, 203 and 204 described above, and the key input device 202, 203 or 204 that is not included may be implemented in other forms, such as soft keys, on the display 220. The connector hole 209 may accommodate a connector (e.g., USB connector) for transmitting and receiving power and/or data to and from an external electronic device, and may include another connector hole (not shown) that can accommodate a connector for transmitting and receiving an audio signal to and from an external electronic device. The electronic device 400 may further include, for example, a connector cover (not shown) that covers at least a portion of the connector hole 209 and blocks foreign substances from entering the connector hole 209.

The fastening members 250 and 260 may be detachably fastened to at least a portion of the housing 210 by using locking members 251 and 261. The fastening members 250 and 260 may include one or more of a fixing member 252, fixing member fastening holes 253, a band guide member 254, and a band fixing ring 255.

The fixing member 252 may be configured to fix the housing 210 and the fastening members 250 and 260 to a body part (e.g., wrist, or ankle) of the user. The fixing member fastening holes 253 may fix the housing 210 and the fastening members 250 and 260 to a body part of the user in correspondence to the fixing member 252. The band guide member 254 may be configured to limit the range of movement of the fixing member 252 when the fixing member 252 engages with a fixing member fastening hole 253, so that the fastening members 250 and 260 may be fastened in close contact to a body part of the user. The band fixing ring 255 may limit the range of movement of the fastening members 250 and 260 while the fixing member 252 and the fixing member fastening hole 253 are fastened.

Figure 4:
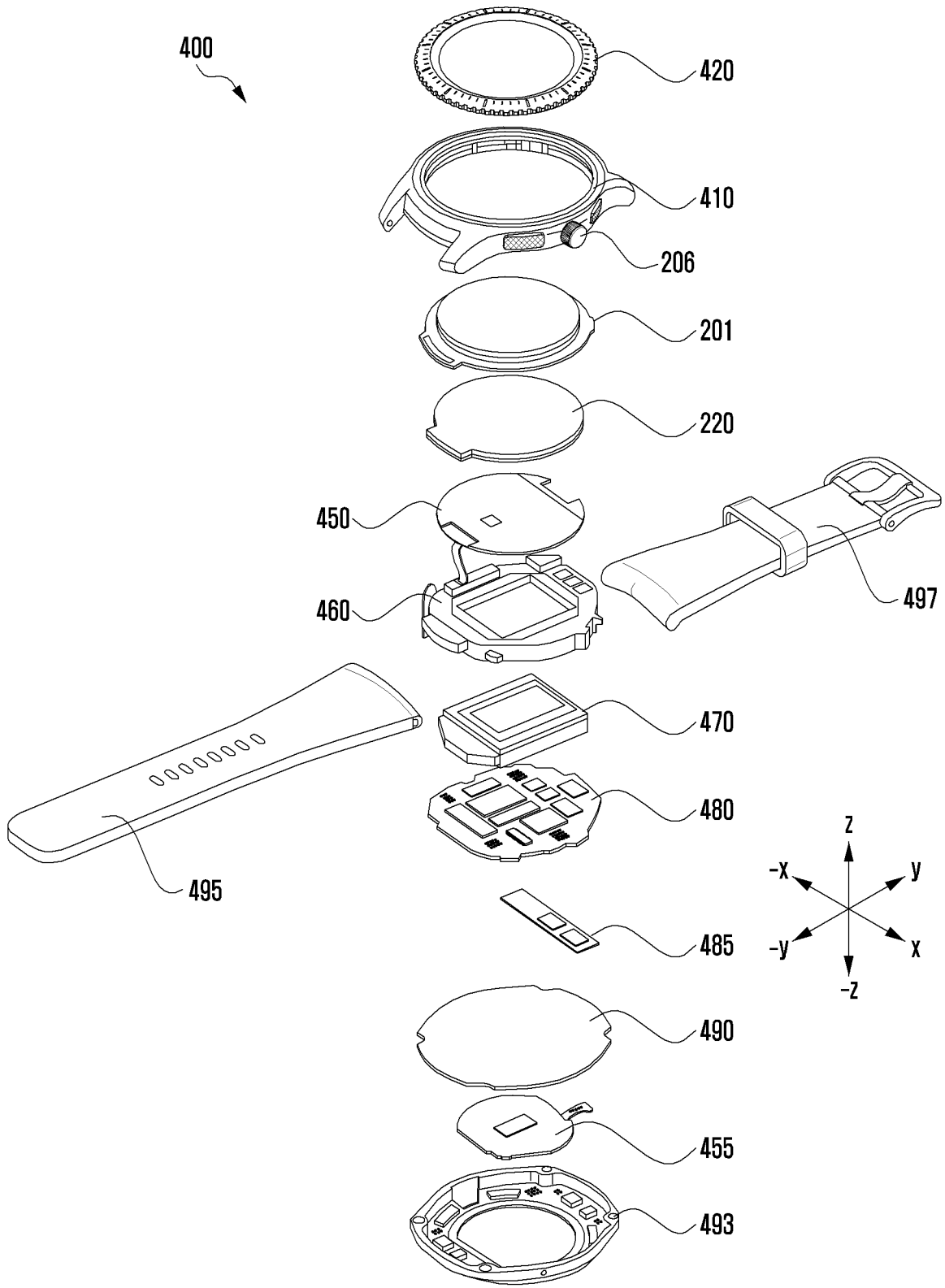
FIG. 4 is an exploded perspective view of the electronic device of FIG. 2 according to certain embodiments.

FIG. 4 is an exploded perspective view of an electronic device according to certain embodiments.

With reference to FIG. 4, the electronic device 400 (e.g., electronic device 400 in FIGS. 2 and 3) may include a hosing 410 (e.g., housing 210 in FIG. 2), a wheel key 202, a front plate 201, a display 220, a first antenna 450, a second antenna 455, a support member 460 (e.g., bracket), a battery 470, a printed circuit board 480, a flexible printed circuit board 485, a sealing member 490, a rear plate 493 (e.g., a rear plate 207 in FIG. 3), and fastening members 495, 497 (e.g., fastening members 250 and 260 in FIGS. 2 and 3). At least one of the components of the electronic device 400 may be identical or similar to at least one of the components of the electronic device 400 of FIG. 2 or 3, and repeated descriptions are omitted herein. In one embodiment, the hosing 410 includes a side bezel structure (e.g., side bezel structure 211). The support member 460 disposed inside the electronic device 400 may be formed to be connected to the hosing 410 or be integrally formed with the hosing 410. The support member 460 may be made of, for example, a metal material and/or a non-metal (e.g., polymer) material. The support member 460 may have one surface coupled to the display 220, or the other surface coupled to the printed circuit board 480. A processor (e.g., processor 120 in FIG. 1), a memory (e.g., memory 130 in FIG. 1), and/or an interface (e.g., interface 177 in FIG. 1) may be mounted on the printed circuit board 480. The flexible printed circuit board 485 may be connected to one surface of the printed circuit board 480. The flexible printed circuit board 485 may be equipped with at least one sensor (e.g., sensor module 176 in FIG. 1) (e.g., biometric sensor and/or an illuminance sensor) and/or a light source.

The battery 470 is a device for supplying power to at least one component of the electronic device 400, and may include, for example, a non-rechargeable primary cell, a rechargeable secondary cell, or a fuel cell. At least a portion of the battery 470 may be disposed substantially on the same plane as, for example, the printed circuit board 480. The battery 470 may be disposed as a single body within the electronic device 400 or may be detachably disposed from the electronic device 400.

The first antenna 450 may be disposed between the display 220 and the support member 241. The first antenna 450 may include, for example, a near field communication (NEC) antenna, a wireless charging antenna, and/or a magnetic secure transmission (MST) antenna. For example, the antenna 243 may perform short-range communication with an external device, wirelessly transmit or receive power required for charging, and transmit a short-range communication signal or a magnetic-based signal including payment data. In another embodiment, an antenna structure may be formed by using portions of the housing 410 and/or the support member 460 or a combination thereof.

The second antenna 455 may be disposed between the printed circuit board 480 and the rear plate 493. The second antenna 455 may include, for example, a near field communication (NEC) antenna, a wireless charging antenna, and/or a magnetic secure transmission (MST) antenna. For example, second antenna 455 may perform short-range communication with an external device, wirelessly transmit or receive power required for charging, and transmit a short-range communication signal or a magnetic-based signal including payment data. In another embodiment, an antenna structure may be formed by using portions of the housing 410 and/or the rear plate 493 or a combination thereof.

The sealing member 490 may be positioned between the hosing 410 and the rear plate 493. The sealing member 490 may be configured to block moisture and foreign matter flowing into the space surrounded by the hosing 410 and the rear plate 207 from the outside.

Figure 5A:
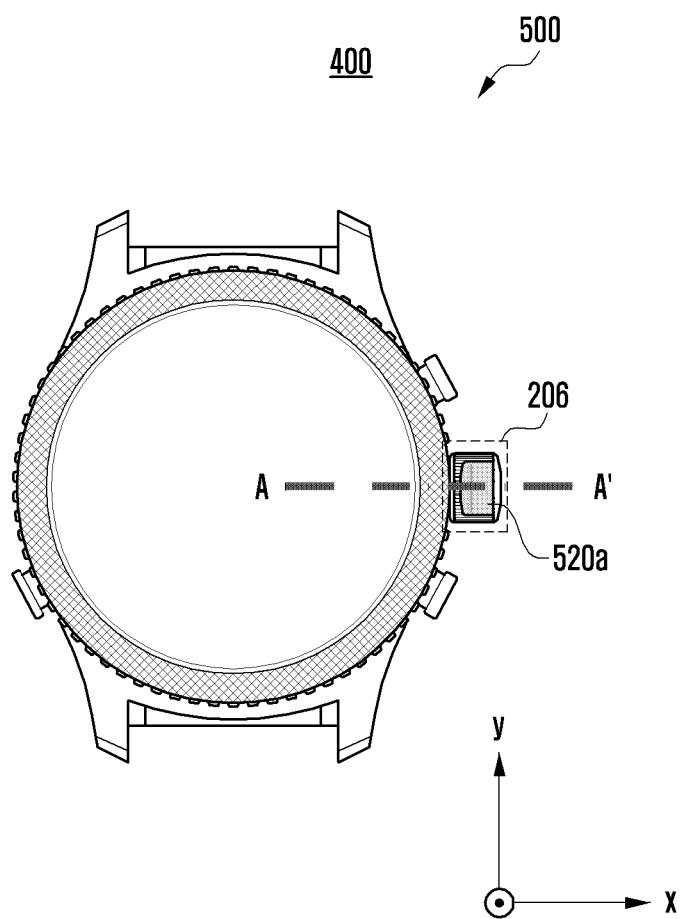
FIG. 5A is a front view of the electronic device according to certain embodiments.
Figure 5B:
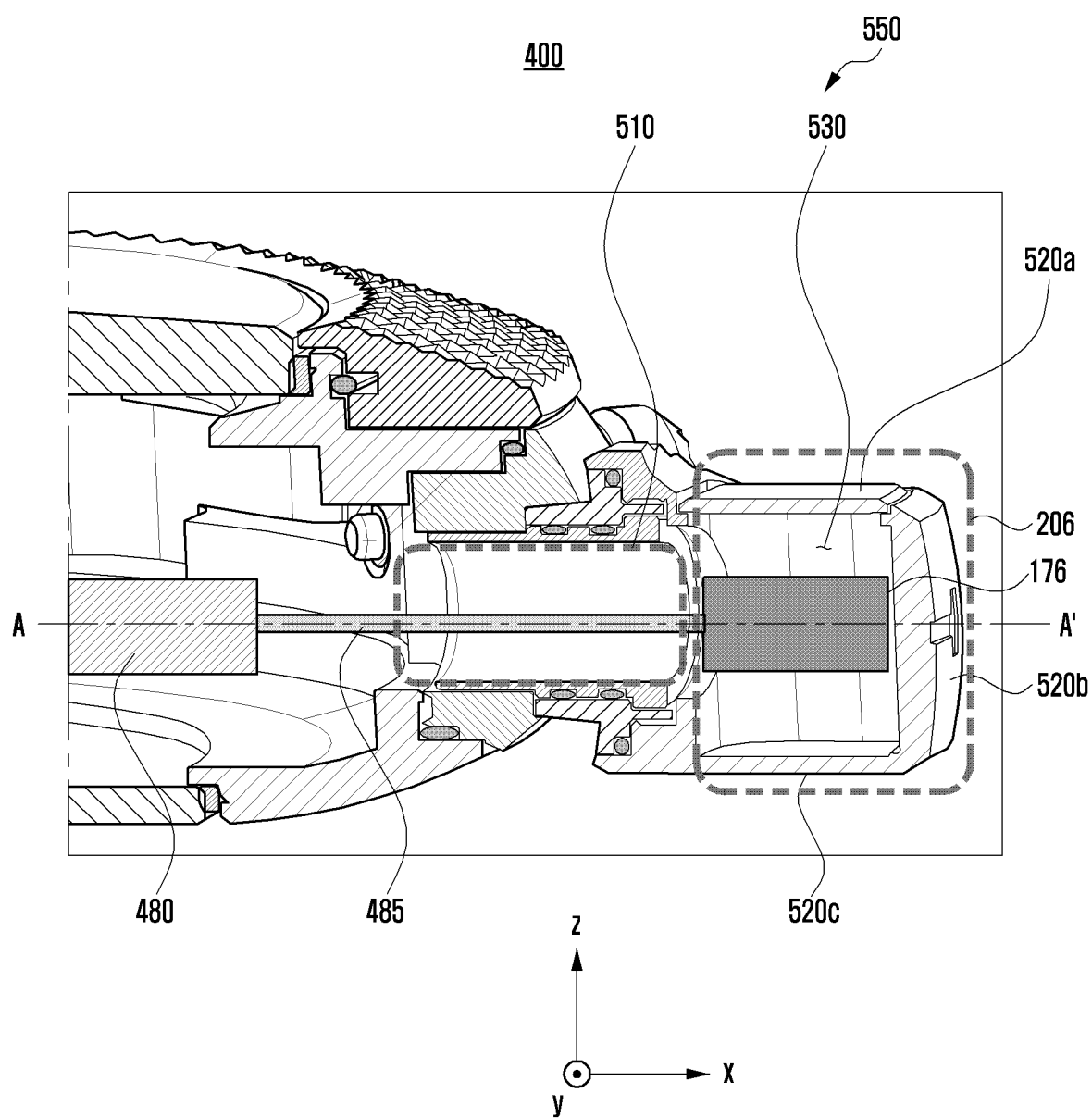
FIG. 5B is a cross-sectional view of the electronic device viewed along line A-A' according to certain embodiments.

FIG. 5A is a front view 500 of the electronic device 400 according to certain embodiments. FIG. 5B is a cross-sectional view 550 of the electronic device 400 viewed along line A-A' according to certain embodiments.

The electronic device 400 includes a housing 210 with a protrusion 206. Various sensors may be disposed in the protrusion 206. The interior of the housing 210 and the interior of the protrusion are connected by a tunnel 510. The housing 210 can include a printed circuit board 480, on which electronic components, such as one or more processors, may be mounted. The sensors module 176 may be connected to the one or more processors by flexible printed circuit board 485 that is disposed in the tunnel 510.

The electronic device 400 including the components and operations described in certain embodiments of this document may include an electronic device that can be in contact with the user's body. In one embodiment, the electronic device 400 may be a wearable electronic device that can be worn on the user's body. Hereinafter, the electronic device 400 in the form of a wrist watch shown in FIGS. 2 to 4 will be described as representative examples. However, the form of the electronic device according to certain embodiments of this document is not limited to the electronic device 400.

With reference to FIGS. 5A and 5B, the electronic device 400 according to certain embodiments may include a main body. The main body may mean a part constituting the external appearance of the electronic device 400. For example, the main body may include a housing structure described with reference to FIGS. 2 to 4 (e.g., the housing 210 including the first surface (or, front surface) 210A, the second surface (or, rear surface) 210B, and the side surface 210C surrounding the space between the first surface 210A and the second surface 210B in FIGS. 2 and 3).

The electronic device 400 may include a printed circuit board 480 disposed in the internal space of the housing 210. For example, a processor (e.g., processor 120 in FIG. 1), a memory (e.g., memory 130 in FIG. 1) and/or an interface (e.g., interface 177 in FIG. 1) may be mounted on the printed circuit board 480. However, this is not limited thereto.

In one embodiment, the electronic device 400 may include a flexible printed circuit board 485 connected to one surface (e.g., surface facing in x-axis direction) of the printed circuit board 480. In one embodiment, a plurality of biometric sensors (e.g., sensor module 176 in FIG. 1) for obtaining user's biometric information may be mounted on the flexible printed circuit board 485. For example, the plurality of biometric sensors may include sensors having a function of obtaining user's biometric information, such as fingerprint, electrocardiogram (ECG), respiration, electromyography (EMG), electrooculogram (EOG), electroencephalogram (EEG), blood glucose, saturation of peripheral oxygen ($SpO_2$), photoplethysmography (PPG), heart rate monitoring (HRM), and/or body temperature.

In the following examples according to certain embodiments, the plurality of biometric sensors mounted on the flexible printed circuit board 485 will be described on the assumption that they are a fingerprint sensor and a heart rate sensor.

This is not limited thereto, and a light source and/or an illuminance sensor may be further mounted on the flexible printed circuit board 485 in certain embodiments.

A plurality of sensors (e.g., plural biometric sensors and/or illuminance sensor) mounted on the flexible printed circuit board 485 may be electrically connected to the processor 120 mounted on the printed circuit board 480. As the plural sensors (e.g., plural biometric sensors and/or illuminance sensor) mounted on the flexible printed circuit board 485 are electrically connected to the processor 120 mounted on the printed circuit board 480, the processor 120 may obtain the user's biometric information and/or detect the proximity of an external object (e.g., body portion of the user) through the plural sensors.

The electronic device 400 may include a protrusion 206 (e.g., structure) that protrudes from one side of the housing 210 and includes an internal space 530. In one embodiment, at least some of the outer shape of the protrusion 206 may be made of a transparent window. For example, the protrusion 206 may include a first surface 520a (e.g., first surface 520a facing in z-axis direction), a second surface 520b facing in a direction perpendicular to the first surface 520a (e.g., second surface 520b facing in x-axis direction), and a third surface 520c facing in a direction perpendicular to the second surface 520b (e.g., third surface 520c facing in negative z-axis direction). In other words, at least a portion of the first surface 520a, the second surface 520b, and/or the third surface 520c of the protrusion 206 may be made of a light-transmitting material that transmits light, for example, a window.

The electronic device 400 may include a hole 510 (e.g., tunnel) connecting the housing 210 and the protrusion 206.

At least a portion of the flexible printed circuit board 485 connected to one surface (e.g., surface facing in x-axis direction) of the printed circuit board 480 may pass through the hole 510 to be disposed in the internal space 530 of the protrusion 206. For example, the at least a portion of the flexible printed circuit board 485 disposed in the internal space 530 of the protrusion 206 may be a region in which a plurality of sensors (e.g., plural biometric sensors and/or illuminance sensor) are disposed. In other words, at least a portion of the flexible printed circuit board 485 (e.g., region in which a plurality of sensors are disposed) may be disposed to be spaced apart, in the internal space 530 of the protrusion 206, from the first surface 520a, the second surface 520b, and/or the third surface 520c forming the outer shape of the protrusion 206.

In certain embodiments, an external object, for example, a body portion of the user, may be positioned on the outer shape of the protrusion 206 made of a window, for example, on the first surface 520a, the second surface 520b, and/or the third surface 520c. The body portion of the user may include a finger and/or a wrist of the user. When a body portion of the user is positioned on the outer shape of the protrusion 206 made of a window, for example, on the first surface 520a, the second surface 520b, and/or the third surface 520c, user's biometric information may be obtained through biometric sensors (e.g., fingerprint sensor and/or heart rate sensor) disposed in the internal space 530 of the protrusion 206. For example, user's biometric information may include fingerprint information and/or heart rate information of the user.

In certain embodiments, based on a body portion of the user positioned on the outer shape of the protrusion 206 made of a light-transmitting material such as a window, for example, on the first surface 520a, the second surface 520b, and/or the third surface 520c, the protrusion 206 may operate as a biometric recognition module that obtains user's biometric information through plural biometric sensors mounted on the flexible printed circuit board 485 disposed in the internal space 530 of the protrusion 206. Hereinafter, the protrusion 206 according to certain embodiments may be referred to as a biometric recognition module.

Certain embodiments, regarding the structure of the flexible printed circuit board 485 including a plurality of sensors disposed in the internal space 530 of the protrusion 206 according to certain embodiments, will be described with reference to FIGS. 6 to 8 below.

Figure 6:
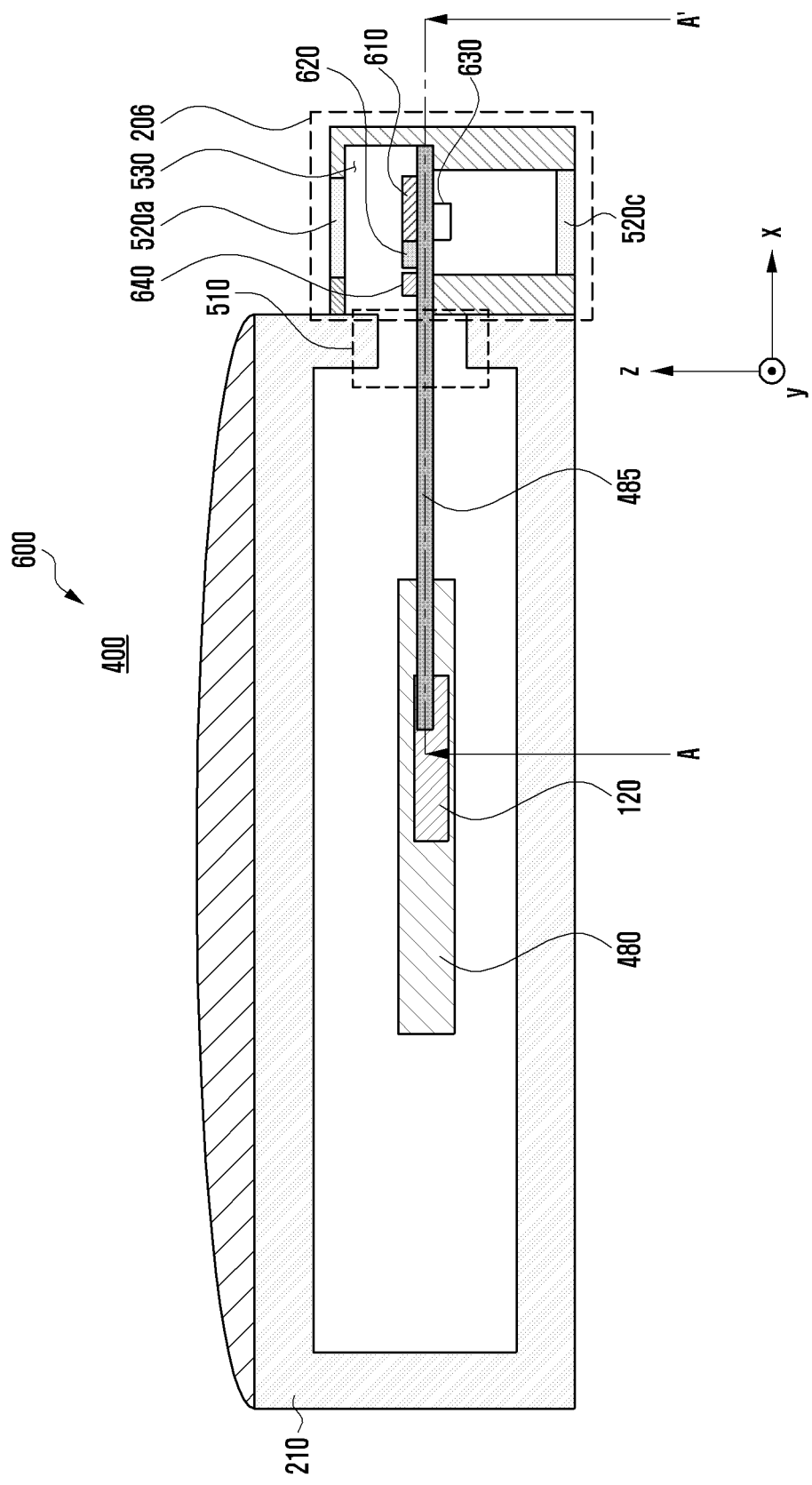
FIG. 6 is a cross-sectional view of the electronic device viewed along line A-A' in FIG. 5A according to certain embodiments.

FIG. 6 is a cross-sectional view 600 of the electronic device 400 viewed along line A-A' in FIG. 5A according to certain embodiments.

With reference to FIG. 6, the electronic device 400 may include a housing 210 that includes a first surface, a second surface, and a side surface surrounding the space between the first surface 210A and the second surface 210B.

The electronic device 400 may include a printed circuit board 480 disposed in the internal space of the housing 210.

In one embodiment, the electronic device 400 may include a flexible printed circuit board 485 connected to one surface (e.g., surface facing in x-axis direction) of the printed circuit board 480. A plurality of sensors may be mounted on the flexible printed circuit board 485. The plurality of sensors may include fingerprint sensor, electrocardiogram (ECG) sensor, electromyography (EMG) sensor, electrooculogram (EOG) sensor, electroencephalogram (EEG) sensor, blood glucose sensor, oxygen saturation ($SpO_2$) sensor, photoplethysmography (PPG) sensor, heart rate (HRM) sensor, and/or illuminance sensor.

In the description of FIG. 6 according to certain embodiments, it is assumed that the plurality of sensors mounted on the flexible printed circuit board 485 are a fingerprint sensor 610, a heart rate sensor 630, and an illuminance sensor 640. For example, the fingerprint sensor 610 and the illuminance sensor 640 may be mounted on the first surface (e.g., first surface facing in z-axis direction) of the flexible printed circuit board 485. The heart rate sensor 630 may be mounted on the second surface of the flexible printed circuit board 485 (e.g., second surface facing in a direction (e.g., negative z-axis direction) opposite to the direction in which the first surface of the flexible printed circuit board 485 faces (e.g., z-axis direction)). Without being limited thereto, a light source 620 may be further mounted on the first surface (e.g., first surface facing in z-axis direction) of the flexible printed circuit board 485.

The electronic device 400 may include a protrusion 206 (e.g., structure) that protrudes from one side surface of the housing 210 and includes an internal space 530. In one embodiment, at least some of the outer shape of the protrusion 206 may be made of a transparent window. For example, the protrusion 206 may include a first surface 520a, a second surface 520b facing in a direction perpendicular to the first surface 520a, and a third surface 520c facing in a direction perpendicular to the second surface 520b. At least a portion of the first surface 520a, the second surface 520b, and/or the third surface 520c of the structure may be made of a transparent window. As another example, at least a portion of the first surface 520a of the protrusion 206 disposed to be spaced apart from the fingerprint sensor 610 mounted on the first surface (e.g., first surface facing in z-axis direction) of the flexible printed circuit board 485 may be made of a transparent window. At least a portion of the third surface 520c of the protrusion 206 disposed to be spaced apart from the heart rate sensor 630 mounted on the second surface (e.g., second surface facing in negative z-axis direction) of the flexible printed circuit board 485 may be made of a transparent window.

The electronic device 400 may include a hole 510 (e.g., tunnel) connecting the housing 210 and the protrusion 206. At least a portion of the flexible printed circuit board 485 connected to one surface of the printed circuit board 480 may pass through the hole 510 to be disposed in the internal space 530 of the protrusion 206.

When a body portion of the user is positioned on a light-transmitting material, for example, one surface (e.g., first surface 520a and/or third surface 520c) of the protrusion 206, a user's biometric information (e.g., fingerprint information and/or heart rate information) can be obtained through multiple biometric sensors disposed in the internal space 530. Accordingly, the protrusion 206 may operate as a biometric recognition module.

In one embodiment, a plurality of sensors (e.g., fingerprint sensor 610, heart rate sensor 630, and/or illuminance sensor 640) mounted on the first surface and the second surface of the flexible printed circuit board 485 may be electrically connected to the processor 120 mounted on the printed circuit board 480. In one embodiment, the processor 120 may detect whether an external object approaches the first surface 520a of the protrusion 206 based on a sensor signal obtained through the illuminance sensor 640. For example, the external object may include a body portion of the user such as a finger or a wrist.

Upon detecting by the illuminance sensor 640 that an external object (e.g., user's finger) is located on the first surface 520a of the protrusion 206, the processor 120 may activate a biometric sensor (e.g., fingerprint sensor 610). For example, at least a portion of the first surface 520a may be made of a light-transmitting material. The light transmitting material may be, for example, a transparent window so as to receive light that is emitted by the light source 620. The light may be emitted by the light source 620 to an external object (e.g., user's finger) on the first surface 520a and reflected by the external object. In one embodiment, when an external object is located on the first surface 520a, light generated from the light source 620 may be irradiated toward the external object. The fingerprint sensor 610 may receive light reflected from the external object. The fingerprint sensor 610 may obtain user's fingerprint information based on light reflected from the external object.

The foregoing describe detecting an external object using an illuminance sensor, but the disclosure is not limited thereto. For example, the illuminance sensor 640 may measure ambient brightness. The processor 120 may adjust the brightness of the display (e.g., display module 160 in FIG. 1 or display 220 in FIG. 4) based on an ambient brightness value measured through the illuminance sensor 640.

In one embodiment, when detecting a user input for obtaining user's heart rate information, the processor 120 may activate the heart rate sensor 630. At least a portion of the third surface 520c may be made of a light-transmitting material, for example, a transparent window. When the user wears the electronic device 400, the third surface 520c of the protrusion 206 may be positioned to make contact with a body portion of the user, for example, the back of the user's wrist. The heart rate sensor 630 may include a light emitting part (not shown) that generates incident light and irradiates the light to an external object. The heart rate sensor 630 may also include a light receiving part (not shown, a photodiode, for example) that receives light reflected from the external object. The light emitting part (not shown) of the heart rate sensor 630 may emit light to the back of the user's wrist. The light reflected by back of the user's wrist may be received through the light receiving part (not shown) of the heart rate sensor 630. The heart rate sensor 630 may measure information related to the user's heart rate based on the light received through the light receiving part (not shown).

An electronic device 400 according to certain embodiments may include: a housing 210; a protrusion (e.g., protrusion 206) from a side surface of the housing including a first window (e.g., first window formed on at least a portion of the first surface 520a) and a second window (e.g., second window formed on at least a portion of the third surface 520c), a first board (e.g., printed circuit board 480) disposed inside the housing 210; a second board (e.g., flexible printed circuit board 485) connected to one surface (e.g., surface facing in x-axis direction) of the first board (e.g., printed circuit board 480); a first sensor circuit (e.g., fingerprint sensor 610) mounted on a first surface (e.g., first surface facing in z-axis direction) of the second board (e.g., flexible printed circuit board 485), disposed in the protrusions, and spaced apart from and under the first window; a second sensor circuit (e.g., heart rate sensor 630) mounted on a second surface of the second board (e.g., flexible printed circuit board 485) facing in an opposite direction (e.g., negative z-axis direction) to the first surface (e.g., first surface facing in z-axis direction) of the second board (e.g., flexible printed circuit board 485); and disposed in the protrusion, and spaced apart from and above the second window.

In certain embodiments, the first board may include a printed circuit board 480, and the second board may include a flexible printed circuit board 485.

The electronic device 400 according to certain embodiments may further include a hole 510 connecting an internal space of the housing 210 and an internal space of the protrusion 206.

In certain embodiments, the second board (e.g., flexible printed circuit board 485) may pass through the hole 510 from one surface of the first board (e.g., printed circuit board 480) and be disposed in the internal space 530 of the protrusion 206.

In certain embodiments, the first window (e.g., first window formed on at least a portion of the first surface 520a) of the protrusion 206 may be configured to contact a finger of the user, and the second window (e.g., second window formed on at least a portion of the third surface 520c) of the protrusion 206 may be formed to contact a wrist of the user.

The electronic device 400 according to certain embodiments may further include an illuminance sensor 640 and/or a light source 620 mounted on the first surface of the second board (e.g., flexible printed circuit board 485).

In certain embodiments, the first sensor circuit (e.g., fingerprint sensor 610) and the second sensor circuit (e.g., heart rate sensor 630) mounted on the second board (e.g., flexible printed circuit board 485) may be electrically connected to a processor 120 mounted on the first board (e.g., printed circuit board 480).

In certain embodiments, the processor 120 may be configured to: detect whether a body portion of the user is placed on the first window (e.g., first window formed on at least a portion of the first surface 520a) through the illuminance sensor 640; when the body portion of the user is placed on the first window, activate the first sensor circuit (e.g., fingerprint sensor 610) and/or the second sensor circuit (e.g., heart rate sensor 630); and obtain biometric information of the user through the first sensor circuit (e.g., fingerprint sensor 610) and/or the second sensor circuit (e.g., heart rate sensor 630).

In certain embodiments, the first sensor circuit may include a fingerprint sensor 610, and the processor 120 may be configured to: emit, based on detecting a finger of the user on the first window (e.g., first window formed on at least a portion of the first surface 520a), light to the user's finger through the light source 620; and obtain fingerprint information of the user based on receiving the emitted light that has been reflected by the user's finger detected on the first window through the fingerprint sensor 610.

In certain embodiments, when the fingerprint sensor 610 is an optical fingerprint sensor, a lens may be applied to the first window (e.g., first window formed on at least a portion of the first surface 520a) and/or the second window (e.g., second window formed on at least a portion of the third surface 520c) to increase the area for concentrating light reflected by the finger.

In certain embodiments, the second sensor circuit may include a heart rate sensor 630, and the processor 120 may be configured to obtain heart rate information of the user based on emitting light toward the user's wrist through a light emitting part of the heart rate sensor 630 and receiving the emitted light that has been reflected by the user's wrist through a light receiving part of the heart rate sensor 630.

In certain embodiments, the flexible printed circuit board 485 may be supported laterally in the protrusion 206.

Figure 7:
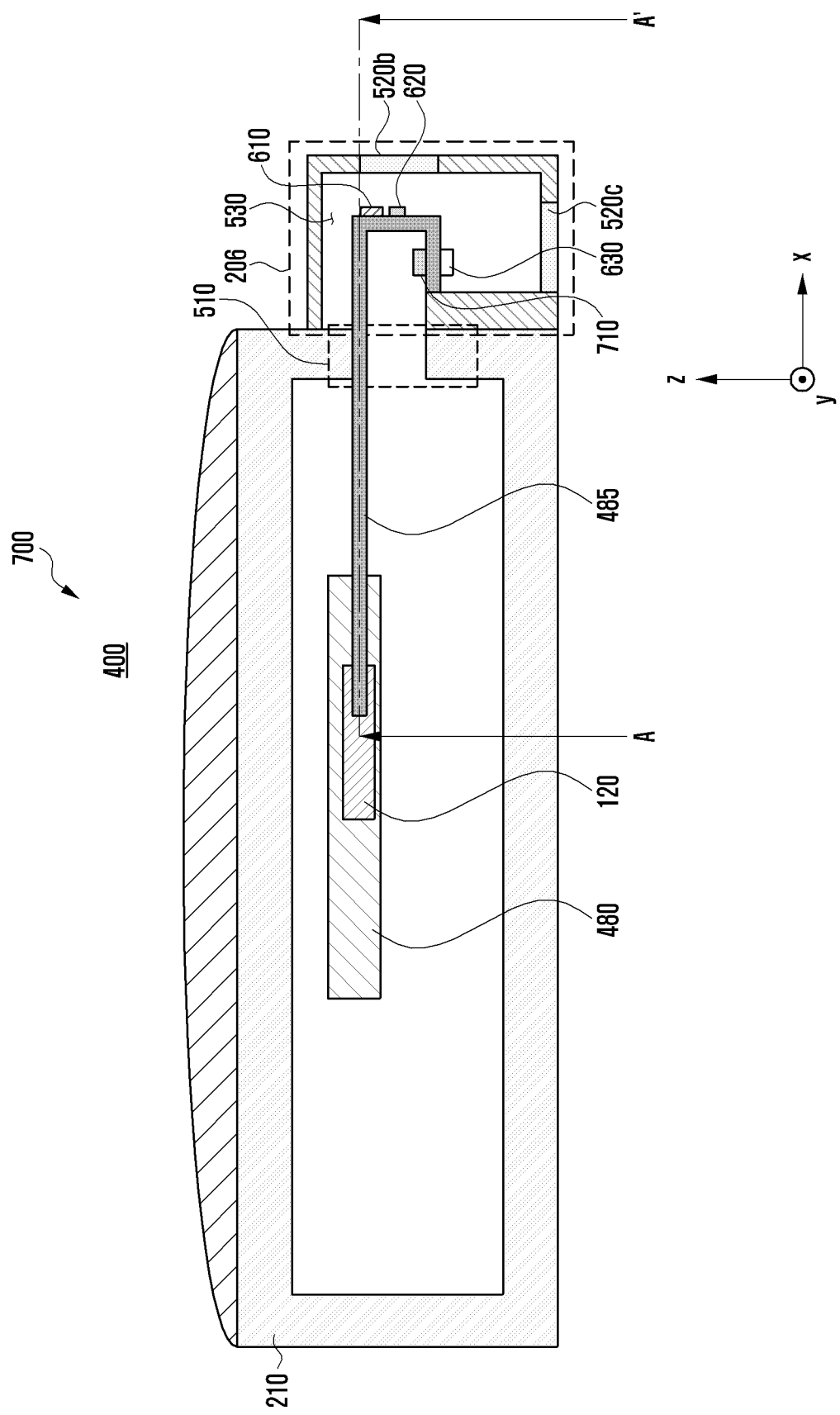
FIG. 7 is a cross-sectional view of the electronic device viewed along line A-A' in FIG. 5A according to certain embodiments.

FIG. 7 is a cross-sectional view 700 of the electronic device 400 viewed along line A-A' in FIG. 5A according to certain embodiments.

In describing the components of the electronic device 400 shown in FIG. 7, the same reference symbols are assigned to the components substantially the same as those of the electronic device 400 described above in FIG. 6, and detailed descriptions thereof may be omitted.

With reference to FIG. 7, the electronic device 400 may include a printed circuit board 480 disposed in the internal space of the housing 210. The electronic device 400 may include a flexible printed circuit board 485 connected to one surface of the printed circuit board 480.

In one embodiment, the electronic device 400 may include a protrusion 206 that protrudes from one side surface of the housing 210 and includes an internal space 530. In one embodiment, at least a portion of the outer shape of the protrusion 206, for example, the first surface 520a, the second surface 520b, and/or the third surface 520c may be made of a transparent window.

In one embodiment, the electronic device 400 may include a hole 510 (e.g., tunnel) connecting an internal space the housing 210 and the internal space 530 of the protrusion 206. At least a portion of the flexible printed circuit board 485 connected to one surface of the printed circuit board 480 may pass through the hole 510 to be disposed in the internal space 530 of the protrusion 206. For example, the flexible printed circuit board 485 may be disposed in the internal space 530 of the protrusion 206 while being folded at least once. For instance, the flexible printed circuit board 485 may include a first surface facing in a first direction (e.g., z-axis direction), a second surface facing in a second direction (e.g., x-axis direction) perpendicular to the first direction (e.g., z-axis direction), and a third surface facing in a third direction (e.g., negative z-axis direction) perpendicular to the second direction (e.g., x-axis direction). The flexible printed circuit board 485 may be formed in an inverted '☐' shape, and may be disposed in the internal space 530 of the protrusion 206.

Based on a body portion of the user (e.g., user's finger and/or wrist) making contact on the outer shape, for example, the first surface 520a, the second surface 520b, and/or the third surface 520c, the protrusion 206 may operate as a biometric recognition module that obtains biometric information of the user through a plurality of biometric sensors mounted on the flexible printed circuit board 485.

In one embodiment, the fingerprint sensor 610 may be mounted on the second surface (e.g., second surface facing in second direction (e.g., x-axis direction)) of the flexible printed circuit board 485. A light source 620 may be further mounted on the second surface of the flexible printed circuit board 485. A heart rate sensor 630 may be mounted on the third surface (e.g., third surface facing in third direction (e.g., negative z-axis direction)) of the flexible printed circuit board 485.

In one embodiment, the flexible printed circuit board 485 may further include a magnet 710 (e.g., magnetic material) mounted at a position corresponding to the heart rate sensor 630 in a fourth surface (e.g., fourth surface facing in first direction (e.g., z-axis direction)) opposite to the third surface of the flexible printed circuit board 485. The magnet 710 may serve to fix the heart rate sensor 630 to prevent movement. For example, the heart rate sensor 630 and the magnet 710 may be mounted so that their central axes coincide. This prevents the heart rate sensor 630 from moving on the flexible printed circuit board 485, and provides improved mounting stability.

In FIG. 7 according to certain embodiments, the protrusion 206 may be implemented to be pushable. When an input signal to the protrusion 206 is detected, the processor 120 may activate a plurality of biometric sensors (e.g., fingerprint sensor 610 and/or heart rate sensor 630) to obtain user's biometric information. In one embodiment, the input signal to the protrusion 206 may include a signal caused by a body portion (e.g., finger) of the user physically pushing the second surface 520b of the protrusion 206 toward the housing 210 (or, main body) of the electronic device 400 (e.g., in negative x-axis direction).

An electronic device 400 according to certain embodiments may include: a housing 210; a protrusion (e.g., protrusion 206) from a side surface of the housing including a first window (e.g., first window formed on at least a portion of the second surface 520b) and a second window (e.g., second window formed on at least a portion of the third surface 520c); a first board (e.g., printed circuit board 480) disposed inside the housing 210; a second board (e.g., flexible printed circuit board 485) connected to one surface of the first board, and including a first surface (e.g., first surface facing in z-axis direction), a second surface in a direction perpendicular to the first surface (e.g., x-axis direction), and a third surface in a direction opposite to the first surface (e.g., negative z-axis direction); a first sensor circuit (e.g., fingerprint sensor 610) mounted on the second surface of the second board and disposed inside the protrusion, wherein the first window is spaced apart on a side of the first sensor circuit; and a second sensor circuit (e.g., heart rate sensor 630) mounted on the third surface of the second board, and disposed inside the protrusion, wherein the second window is spaced part and under the second sensor circuit.

The electronic device 400 according to certain embodiments may further include a magnet 710 mounted at a position corresponding to the second sensor circuit (e.g., heart rate sensor 630) in a fourth surface opposite to the third surface of the second board so that the second sensor circuit (e.g., heart rate sensor 630) mounted on the third surface of the second board (e.g., flexible printed circuit board 485) is fixed on the second board.

The electronic device 400 according to certain embodiments may further include a processor 120 mounted on the first board (e.g., printed circuit board 480); and, when the protrusion 206 is implemented to be pushable, the processor 210 may be configured to, in response to detection of a push signal to the protrusion 206, activate the first sensor circuit (e.g., fingerprint sensor 610) and/or the second sensor circuit (e.g., heart rate sensor 630), and obtain user's biometric information through the first sensor circuit (e.g., fingerprint sensor 610) and/or the second sensor circuit (e.g., heart rate sensor 630).

The electronic device 400 according to certain embodiments may further include a light source 620 mounted on the second surface of the second board (e.g., flexible printed circuit board 485).

Figure 8:
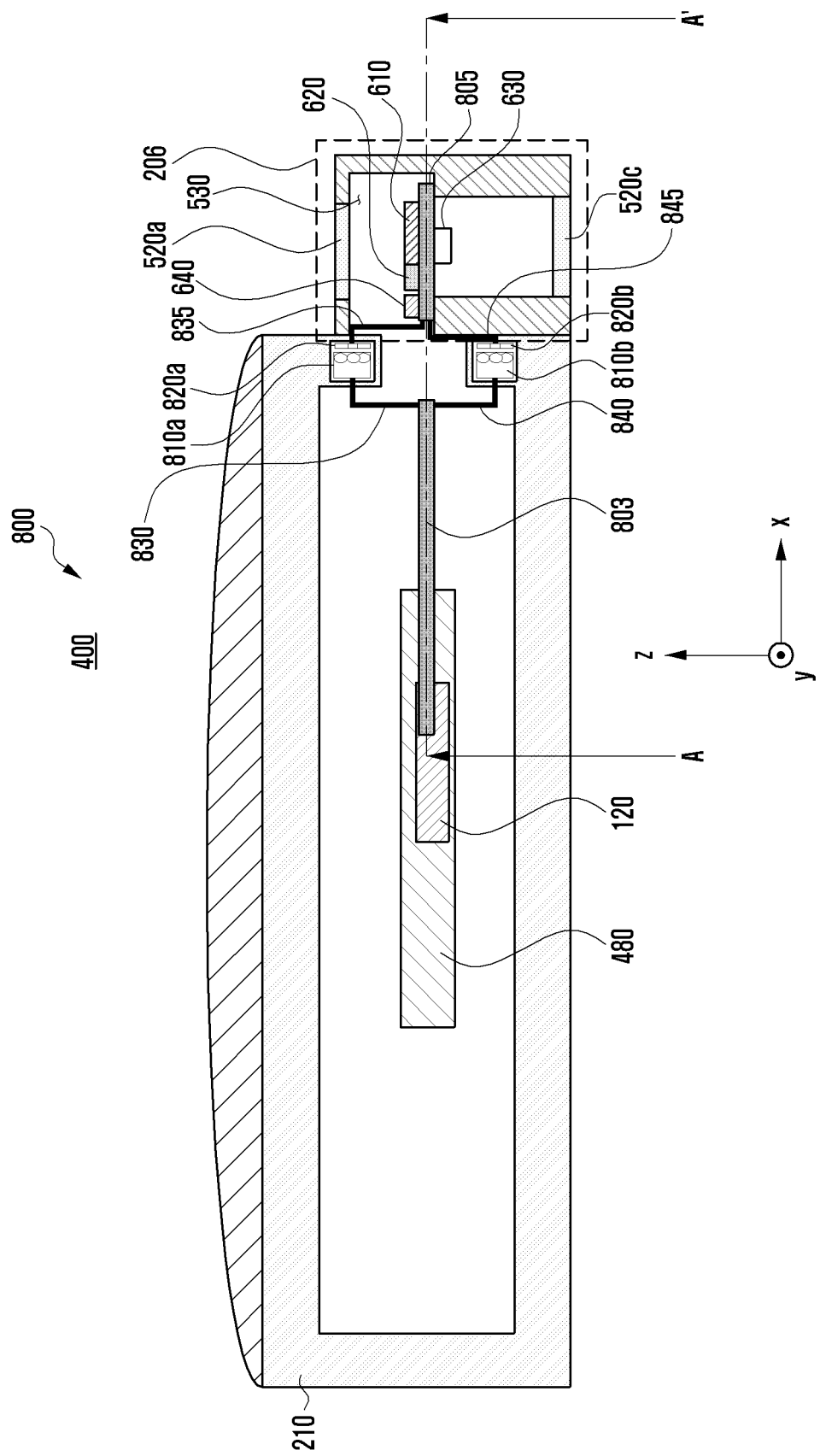
FIG. 8 is a cross-sectional view of the electronic device viewed along line A-A' in FIG. 5A according to certain embodiments.

FIG. 8 is a cross-sectional view 800 of the electronic device 400 viewed along line A-A' in FIG. 5A according to certain embodiments.

In describing the components of the electronic device 400 shown in FIG. 8, the same reference symbols are assigned to the components substantially the same as those of the electronic device 400 described above in FIG. 6, and detailed descriptions thereof may be omitted.

With reference to FIG. 8, the electronic device 400 according to certain embodiments may include a protrusion 206 (e.g., biometric recognition module or structure) that is formed to protrude from one side surface of the housing 210 and includes an internal space 530. In certain embodiments, the protrusion 206 may be configured to be rotatable. When the protrusion 206 is configured to be rotatable, the protrusion 206 may operate as an input means according to the design method. In one embodiment, at least a portion of the outer shape of the protrusion 206, for example, the first surface 520a, the second surface 520b, and/or the third surface 520c may be made of a transparent window.

In certain embodiments, the electronic device 400 may include a printed circuit board 480 disposed in the internal space of the housing 210. The electronic device 400 may include a first flexible printed circuit board 803 (e.g., flexible printed circuit board 485 in FIGS. 4 to 7) connected to one surface (e.g., surface facing in x-axis direction) of the printed circuit board 480.

In FIGS. 4 and 7 described above according to certain embodiments, it has been described that a plurality of sensors and/or light sources are mounted on the flexible printed circuit board 485 connected to one surface (e.g., surface facing in x-axis direction) of the printed circuit board 480 through a hole (e.g., hole 510 in FIGS. 5 to 7), but the disclosure is not limited thereto. In FIG. 8 according to certain embodiments, the electronic device 400 may further include a second flexible printed circuit board 805 disposed in the internal space 530 of the protrusion 206 separately from the first flexible printed circuit board 803. A plurality of sensors and/or light sources may be mounted on the second flexible printed circuit board 805. For example, a fingerprint sensor 610, a light source 620, and/or an illuminance sensor 640 may be mounted on a first surface (e.g., first surface facing in z-axis direction) of the second flexible printed circuit board 805. A heart rate sensor 630 may be mounted on a second surface of the second flexible printed circuit board 805 (e.g., second surface facing in the negative z-axis direction opposite to the direction of the first surface).

In certain embodiments, a plurality of connection members may be positioned between the first flexible printed circuit board 803 (e.g., flexible printed circuit board 485 in FIGS. 4 to 7) and the second flexible printed circuit board 805. The second flexible printed circuit board 805 may be electrically connected to the first flexible printed circuit board 803 through the plural connection members. For example, the plural connection members may be made of conductors so as to electrically connect the first flexible printed circuit board 803 and the second flexible printed circuit board 805. For instance, the plural connection members may include a plurality of conductive members and a plurality of conductive pads. For example, the conductive members may include a C clip (e.g., C-shaped spring), a pogo-pin, a spring, conductive phorone, conductive rubber, conductive tape, or a copper connector. However, they are not limited thereto.

In certain embodiments, the plural connection members may include a first conductive member 810a, a second conductive member 810b, a first conductive pad 820a, and a second conductive pad 820b.

In certain embodiments, the first conductive member 810a and the first conductive pad 820a may be bonded to each other to be integrally formed. The first flexible printed circuit board 803 and the first conductive member 810a may be electrically connected through a first conductive path 830, and the first conductive pad 820a and the second flexible printed circuit board 805 may be electrically connected through a second conductive path 835. Accordingly, the first flexible printed circuit board 803 and the second flexible printed circuit board 805 may be electrically connected through the first conductive member 810a, the first conductive path 830, the first conductive pad 820a, and the second conductive path 835.

In certain embodiments, the second conductive member 810b and the second conductive pad 820b may be bonded to each other to be integrally formed. The first flexible printed circuit board 803 and the second conductive member 810b may be electrically connected through a third conductive path 840, and the second conductive pad 820b and the second flexible printed circuit board 805 may be electrically connected through a fourth conductive path 845. Accordingly, the first flexible printed circuit board 803 and the second flexible printed circuit board 805 may be electrically connected through the second conductive member 810b, the third conductive path 840, the second conductive pad 820b, and the fourth conductive path 845.

In certain embodiments, as the first flexible printed circuit board 803 and the second flexible printed circuit board 805 are electrically connected through the plural connection members (e.g., first conductive member 810a, first conductive pad 820a, second conductive member 810b, and second conductive pad 820b), the first conductive path 830, the second conductive path 835, the third conductive path 840, and the fourth conductive path 845, the processor 120 mounted on the printed circuit board 480 connected to the first flexible printed circuit board 803 may be electrically connected to the plural sensors (e.g., plural biometric sensors (e.g., fingerprint sensor 610, heart rate sensor 630), and/or illuminance sensor 640) mounted on the second flexible printed circuit board 805. As the processor 120 mounted on the printed circuit board 480 is electrically connected to the plural sensors (e.g., fingerprint sensor 610, heart rate sensor 630), and/or illuminance sensor 640) mounted on the second flexible printed circuit board 805, the processor 120 may obtain user's biometric information (e.g., fingerprint information and/or heart rate information) through the plural sensors (e.g., fingerprint sensor 610 and/or heart rate sensor 630), and/or may detect proximity of an external object (e.g., body portion of the user) on the window (e.g., first surface 520a and/or third surface 520c of the protrusion 206) through the illuminance sensor 640.

An electronic device 400 according to certain embodiments may include: a housing 210; a protrusion (e.g., protrusion 206) from a side surface of the housing including a first window (e.g., first window formed on at least a portion of the first surface 520a) and a second window (e.g., second window formed on at least a portion of the third surface 520c), a first board (e.g., printed circuit board 480) disposed inside the housing 210; a second board (e.g., first flexible printed circuit board 803) connected to one surface of the first board; a third board (e.g., second flexible printed circuit board 805) electrically connected to the second board through a plurality of connection members; a first sensor circuit (e.g., fingerprint sensor 610) disposed on a first surface (e.g., first surface facing in z-axis direction) of the third board, and wherein the first window is spaced apart above the first sensor circuit; and a second sensor circuit (e.g., heart rate sensor 630) disposed on a second surface (e.g., second surface facing in negative z-axis direction being opposite to the direction of the first surface) of the third board, and wherein the second window disposed to be spaced apart under the second sensor circuit.

In certain embodiments, the plurality of connection members may include a plurality of conductive members and a plurality of conductive pads.

In certain embodiments, the plurality of conductive members may include a first conductive member 810a and a second conductive member 810b, and the plurality of conductive pads may include a first conductive pad 820a and a second conductive pad 820b; the first conductive member 810a and the first conductive pad 820a may be bonded to each other to be integrally formed, and the second conductive member 810b and the second conductive pad 820b may be bonded to each other to be integrally formed.

In certain embodiments, the electronic device 400 may further include: a first conductive connection member 830 electrically connecting the second board (e.g., first flexible printed circuit board 803) and the first conductive member 810a; a second conductive connection member 835 electrically connecting the first conductive pad 820a and the third board (e.g., second flexible printed circuit board 805); a third conductive connection member 840 electrically connecting the second board (e.g., first flexible printed circuit board 803) and the second conductive member 810b; and a fourth conductive connection member 845 electrically connecting the second conductive pad 820b and the third board (e.g., second flexible printed circuit board 805).

In certain embodiments, the electronic device 400 may further include a processor 120 mounted on the first board (e.g., printed circuit board 480), and the processor 120 may be electrically connected to the first sensor circuit (e.g., fingerprint sensor 610) and the second sensor circuit (e.g., heart rate sensor 630) mounted on the third board (e.g., second flexible printed circuit board 805) through the second board (e.g., first flexible printed circuit board 803), the first conductive connection member 830, the second conductive connection member 835, the third conductive connection member 840, and the fourth conductive connection member 845.

Figure 9:
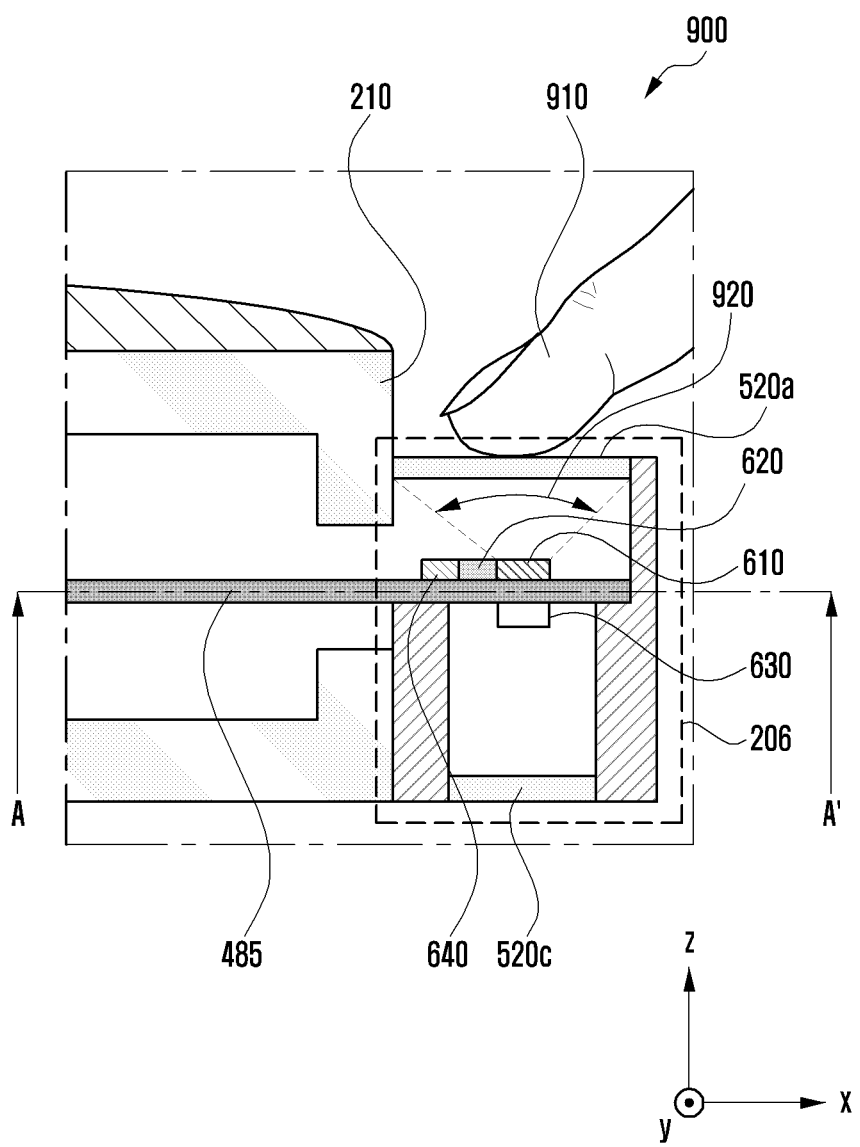
FIG. 9 is a view for explaining a window formed on one surface of a protrusion when the fingerprint sensor is made of an optical fingerprint sensor according to certain embodiments.

FIG. 9 is a view 900 for explaining a window formed on one surface of the protrusion 206 when the fingerprint sensor 610 is made of an optical fingerprint sensor according to certain embodiments.

In describing the components of the electronic device 400 shown in FIG. 9, the same reference symbols are assigned to the components substantially the same as those of the electronic device 400 described above in FIG. 6, and detailed descriptions thereof may be omitted.

With reference to FIG. 9, the electronic device 400 may include a protrusion 206 (e.g., biometric recognition module or structure) that is formed to protrude from one side surface of the housing 210 and includes an internal space 530. In one embodiment, at least a portion of the outer shape of the protrusion 206, for example, the first surface 520a, the second surface 520b, and/or the third surface 520c may be made of a transparent window.

In certain embodiments, the electronic device 400 may include a printed circuit board 480 disposed in the internal space of the housing 210. The electronic device 400 may include a flexible printed circuit board 485 connected to one surface (e.g., surface facing in x-axis direction) of the printed circuit board 480. A fingerprint sensor 610 may be mounted on the first surface (e.g., first surface facing in z-axis direction) of the flexible printed circuit board 485, and a heart rate sensor 630 may be mounted on the second surface (e.g., second surface facing in negative z-axis direction) of the flexible printed circuit board 485.

In certain embodiments, the fingerprint sensor 610 mounted on the first surface of the flexible printed circuit board 485 may be an optical fingerprint sensor.

In certain embodiments, to widen the angle-of-view 920, a lens may be applied to the transparent window that forms at least a portion of the outer shape (e.g., first surface 520a, second surface 520b, and/or third surface 520c) of the protrusion 206. For example, when a user's finger 910 is positioned on the outer shape, for example, the first surface 520a, the second surface 520b, and/or the third surface 520c of the protrusion 206, at least a portion of the outer shape being made of a window, light emitted from the light source 620 may pass through the window forming one surface of the protrusion 206 on which the user's finger 910 is positioned and may be reflected by the user's finger 910. The light reflected by the user's finger 910 may be collected on the transparent window to which the lens is applied, and may be received by the light receiving part of the fingerprint sensor 610. As the lens is applied to the window that forms at least a portion of the outer shape of the protrusion 206 (e.g., first surface 520a, second surface 520b, and/or third surface 520c), the area (e.g., angle-of-view 920) that can collect the light reflected by the user's finger 910 may be widened, and hence a larger area of the user's finger 910 can be captured compared to a case where no lens is applied to the window. As a large area of the user's finger 910 can be captured, the recognition rate of the fingerprint sensor 610 may be increased.

In the electronic device 400 of FIGS. 2 to 9 according to certain embodiments, a plurality of sensors (e.g., fingerprint sensor 610, heart rate sensor 630, and/or illuminance sensor 640) capable of measuring user's biometric information can be disposed in the internal space 530 of the protrusion 206 formed to protrude from a side surface of the electronic device 400, which can improve the accuracy of biometric recognition. In addition, compared to a related-art case where a plurality of sensors are disposed in the internal space of the electronic device, as a plurality of sensors are disposed in the internal space 530 of the protrusion 206 formed to protrude from a side surface of the electronic device 400 according to certain embodiments of the disclosure, it is possible to realize slimming of the electronic device 400.

Hereinabove, certain embodiments of the disclosure have been shown and described for the purpose of illustration without limiting the subject matter of the disclosure. It should be understood that many variations and modifications of the basic inventive concept described herein will still fall within the spirit and scope of the disclosure as defined in the appended claims and their equivalents.

The invention claimed is:

1. An electronic device comprising:
   a housing;
   a protrusion from a side surface of the housing, the protrusion comprising a first surface facing a first direction and a second surface facing a second direction opposite the first direction;
   a first window forming at least a portion of the first surface of the protrusion;
   a second window forming at least a portion of the second surface of the protrusion;
   a first board disposed inside the housing;
   a second board electrically connected to the first board;
   a first sensor circuit mounted on a first surface of the second board facing the first direction, disposed in the protrusion, and configured to obtain a first biometric signal through the first window; and
   a second sensor circuit mounted on a second surface of the second board facing the second direction, disposed in the protrusion, spaced apart from the second window, and configured to obtain a second biometric signal through the second window,
   wherein a type of the first biometric signal is different from a type of the second biometric signal.

2. The electronic device of claim 1, wherein the first board includes a printed circuit board, and the second board includes a flexible printed circuit board.

3. The electronic device of claim 1, further comprising a hole connecting an internal space of the housing and an internal space of the protrusion.

4. The electronic device of claim 3, wherein the second board passes through the hole from one surface of the first board and is disposed in the internal space of the protrusion.

5. The electronic device of claim 1,
   wherein the first biometric signal comprises a fingerprint of a user; and
   wherein the second biometric signal comprises a heart rate of the user.

6. The electronic device of claim 1, further comprising at least one of an illuminance sensor d/or a light source mounted on the first surface of the second board.

7. The electronic device of claim 6, wherein the first sensor circuit and the second sensor circuit mounted on the second board are electrically connected to a processor mounted on the first board.

8. The electronic device of claim 7, wherein the processor is configured to:
   detect whether a body portion of a user is placed on the first window through the illuminance sensor,
   when the body portion of the user is placed on the first window, activate at least one of the first sensor circuit or the second sensor circuit, and
   obtain at least one of the first biometric signal or second biometric signal through at least one of the first sensor circuit or the second sensor circuit.

9. The electronic device of claim 8, wherein the first sensor circuit includes a fingerprint sensor, and wherein the processor is configured to:
   emit, in response to detecting a finger of the user on the first window, light to the user's finger through the light source; and
   obtain fingerprint information of the user based on receiving, through the fingerprint sensor, the emitted light that has been reflected by the user's finger detected on the first window.

10. The electronic device of claim 9, wherein the fingerprint sensor is an optical fingerprint sensor, and a lens is applied to the first window and/or the second window and configured to increase an area for collecting light reflected by the finger.

11. The electronic device of claim 8,
    wherein the second sensor circuit includes a heart rate sensor; and
    wherein the processor is configured to obtain heart rate information of the user based on emitting light toward a wrist of the user through a light emitting part of the heart rate sensor and receiving the emitted light that has been reflected by the user's wrist through a light receiving part of the heart rate sensor.

12. An electronic device comprising:
    a housing;
    a protrusion from a side surface of the housing, the protrusion comprising a first surface facing a first direction and a second surface facing a second direction perpendicular to the first direction;
    a first window forming at least a portion of the first surface of the protrusion;
    a second window forming at least a portion of the second surface of the protrusion;
    a first board disposed inside the housing;
    a second board electrically connected to the first board, the second board including a first surface facing the first direction, and a second surface facing the second direction;
    a first sensor circuit mounted on the first surface of the second board and disposed inside the protrusion, wherein the first sensor circuit is configured to obtain a first biometric signal through the first window; and
    a second sensor circuit mounted on the second surface of the second board, and disposed inside the protrusion, wherein the second sensor circuit is spaced apart from the second window and configured to obtain a second biometric signal through the second window,
    wherein a type of the first biometric signal is different from a type of the second biometric signal.

13. The electronic device of claim 12, further comprising a magnet that is mounted at a position corresponding to the second sensor circuit in a third surface opposite to the second surface of the second board so as to fix the second sensor circuit mounted on the second surface of the second board on the second board.

14. The electronic device of claim 12, further comprising a processor mounted on the first board, and wherein the protrusion is pushable, and the processor is configured to, in response to detection of a push signal to the protrusion, activate at least one of the first sensor circuit or the second sensor circuit, and obtain at least one biometric information through the at least one of the first sensor circuit or the second sensor circuit.

15. The electronic device of claim 12, further comprising a light source mounted on the first surface of the second board.

16. An electronic device comprising:
a housing;
a protrusion from a side surface of the housing, the protrusion comprising a first surface facing a first direction and a second surface facing a second direction opposite the first direction;
a first window forming at least a portion of the first surface of the protrusion;
second window forming at least a portion of the second surface of the protrusion;
a first board disposed inside the housing;
a second board electrically connected to the first board;
a third board electrically connected to the second board through a plurality of connection members;
a first sensor circuit disposed on a first surface of the third board facing the first direction, and wherein the first sensor circuit is configured to obtain a first biometric signal through the first window; and
a second sensor circuit disposed on a second surface of the third board facing the second direction, and wherein the second sensor circuit disposed to be spaced apart from the second window and configured to obtain a second biometric signal through the second window,
wherein a type of the first biometric signal is different from a type of the second biometric signal.

17. The electronic device of claim 16, wherein the plurality of connection members includes a plurality of conductive members and a plurality of conductive pads.

18. The electronic device of claim 17,
wherein the plurality of conductive members includes a first conductive member and a second conductive member;
wherein the plurality of conductive pads includes a first conductive pad and a second conductive pad; and
wherein the first conductive member and the first conductive pad are bonded to each other to be integrally formed, and the second conductive member and the second conductive pad are bonded to each other to be integrally formed.

19. The electronic device of claim 18, further comprising:
a first conductive connection member to electrically connect the second board and the first conductive member;
a second conductive connection member to electrically connect the first conductive pad and the third board;
a third conductive connection member to electrically connect the second board and the second conductive member; and
a fourth conductive connection member to electrically connect the second conductive pad and the third board.

20. The electronic device of claim 19, further comprising a processor mounted on the first board, and wherein the processor is electrically connected to the first sensor circuit and the second sensor circuit mounted on the third board through the second board, the first conductive connection member, the second conductive connection member, the third conductive connection member, and the fourth conductive connection member.

* * * * *